United States Patent
Bennett et al.

(10) Patent No.: US 11,464,924 B2
(45) Date of Patent: Oct. 11, 2022

(54) RESPIRATORY THERAPY APPARATUS

(71) Applicant: SMITHS MEDICAL INTERNATIONAL LIMITED, Ashford (GB)

(72) Inventors: Paul James Leslie Bennett, Bedfordshire (GB); Robert James Burchell, Hertfordshire (GB); Mohammad Qassim Mohammad Khasawneh, Luton (GB); Mark Charles Oliver, Hertfordshire (GB); Mark Sinclair Varney, Bedfordshire (GB)

(73) Assignee: Smiths Medical International Limited, Ashford (GB)

( * ) Notice: Subject to any disclaimer, the term of this patent is extended or adjusted under 35 U.S.C. 154(b) by 871 days.

(21) Appl. No.: 15/109,559

(22) PCT Filed: Nov. 8, 2014

(86) PCT No.: PCT/GB2014/000456
§ 371 (c)(1),
(2) Date: Jul. 1, 2016

(87) PCT Pub. No.: WO2015/104522
PCT Pub. Date: Jul. 16, 2015

(65) Prior Publication Data
US 2016/0331917 A1 Nov. 17, 2016

(30) Foreign Application Priority Data
Jan. 7, 2014 (GB) ...................................... 1400188

(51) Int. Cl.
*A61M 16/00* (2006.01)
*A63B 23/18* (2006.01)
*A61M 16/20* (2006.01)
*A61M 16/08* (2006.01)
*A63B 71/06* (2006.01)
*A63B 21/008* (2006.01)

(52) U.S. Cl.
CPC .... *A61M 16/0006* (2014.02); *A61M 16/0866* (2014.02); *A61M 16/208* (2013.01);
(Continued)

(58) Field of Classification Search
CPC .. A61M 16/205; A61M 16/208; A61M 16/08; A61M 16/0006; A61M 16/209;
(Continued)

(56) References Cited

U.S. PATENT DOCUMENTS 6,058,932 A * 5/2000 Hughes ............... A61H 23/0236
128/200.24
6,165,105 A 12/2000 Boutellier et al.
(Continued)

FOREIGN PATENT DOCUMENTS

EP 1103287 5/2001
EP 1594105 A1 9/2005
(Continued)

OTHER PUBLICATIONS

PCT International Search Report (PCT/ISA/210) and Written Opinion (PCT/ISA/237) ISA/EP, PCT/GB2014/000456, dated Jan. 27, 2015.

*Primary Examiner* — Joseph D. Boecker
*Assistant Examiner* — Brian T Khong
(74) *Attorney, Agent, or Firm* — Louis Woo

(57) ABSTRACT

Respiratory therapy apparatus includes an oscillating expiratory therapy device and pressure and flow sensors in the patient inlet connected to supply signals to a processor. The processor includes artificial intelligence software to correlate the output signals with prescribed values and control a feedback device that prompts the patient accordingly to adjust use of the device as necessary. The feedback device may be of a visual, audible or tangible kind. The processor
(Continued)

may also automatically adjust a setting dial of the therapy device by means of an actuator.

2 Claims, 4 Drawing Sheets

(52) U.S. Cl.
CPC .......... *A63B 21/0088* (2013.01); *A63B 23/18* (2013.01); *A63B 71/0622* (2013.01); *A61M 2016/003* (2013.01); *A61M 2016/0027* (2013.01); *A61M 2205/50* (2013.01); *A61M 2205/581* (2013.01); *A61M 2205/582* (2013.01); *A61M 2205/583* (2013.01); *A63B 2071/0625* (2013.01); *A63B 2220/56* (2013.01); *A63B 2225/50* (2013.01); *A63B 2225/54* (2013.01)

(58) Field of Classification Search
CPC .................. A61M 16/00; A61M 16/20; A61M 2205/581; A61M 2205/582; A61M 2205/583; A61M 15/0076; A61M 15/0073; A61M 15/0075; A63B 23/18
See application file for complete search history.

(56) References Cited

U.S. PATENT DOCUMENTS

| | | | | |
|---|---|---|---|---|
| 6,581,596 B1* | 6/2003 | Truitt | ................... | A61M 16/00 128/204.18 |
| 2003/0127092 A1* | 7/2003 | Pelerossi | ............... | A61M 16/08 128/200.24 |
| 2003/0189492 A1* | 10/2003 | Harvie | .............. | A61M 16/0051 340/573.1 |
| 2003/0234017 A1* | 12/2003 | Pelerossi | ................. | A61M 16/08 128/201.26 |
| 2007/0113843 A1* | 5/2007 | Hughes | ............. | A61M 16/0057 128/200.24 |
| 2008/0053456 A1* | 3/2008 | Brown | .................. | A61M 16/20 128/207.16 |
| 2008/0178880 A1* | 7/2008 | Christopher | ...... | A61M 16/0051 128/204.23 |
| 2009/0264255 A1* | 10/2009 | Tutsch | ................... | A63B 23/18 482/13 |
| 2010/0101573 A1* | 4/2010 | Foley | .................. | A61M 16/208 128/203.15 |
| 2010/0170512 A1* | 7/2010 | Kuypers | ............... | A61M 16/20 128/204.23 |
| 2011/0290240 A1* | 12/2011 | Meyer | .................... | A61M 11/06 128/200.14 |
| 2012/0304988 A1* | 12/2012 | Meyer | ................. | A61M 16/208 128/203.12 |
| 2014/0260667 A1* | 9/2014 | Berkcan | ................. | G01F 1/66 73/861.28 |
| 2015/0306325 A1* | 10/2015 | Laura Lapoint | .. | A61M 16/0051 128/204.23 |
| 2016/0339202 A1* | 11/2016 | Burchell | ................ | A61M 16/04 |

FOREIGN PATENT DOCUMENTS

| | | |
|---|---|---|
| EP | 1897576 | 3/2008 |
| WO | 94/17369 A1 | 8/1994 |

* cited by examiner

RESPIRATORY THERAPY APPARATUS

This invention relates to a respiratory therapy apparatus and apparatuses of the kind including a device having a mechanism arranged to produce an oscillating resistance to breathing through the device, the therapy device having a plurality of different operation settings.

Patients with respiratory system diseases (such as asthma, COPD, cystic fibrosis or the like) may suffer from hyper-secretion of mucus as a prominent pathophysiological feature. Moreover, those patients with hyper-secretion often also have impaired mucus transport. This imbalance between mucus transport and secretion results in mucus retention in the respiratory system.

Vibratory respiratory positive expiratory pressure (V-PEP) or oscillatory PEP (OPEP) devices are modern devices for applying chest physiotherapy. These devices apply chest physiotherapy by providing an alternating resistance to flow and have been found to be particularly effective. One example of such apparatus is sold under the trade mark ACAPELLA (a registered trade mark of SMITHS MEDICAL) by SMITHS MEDICAL and is described in U.S. Pat. Nos. 6,581,598, 6,776,159, 7,059,324 and 7,699,054. Other vibratory respiratory therapy apparatus is available, such as "QUAKE" manufactured by THAYER, "AEROPEP" manufactured by MONAGHAN, "THERA-PEP" manufactured by SMITHS MEDICAL, "IPV PER-CUSSIONATOR" manufactured by PERCUSSIONAIRE CORP, and the "FLUTTER" and "LUNG FLUTE" devices, amongst others. These devices are used by patients who suffer from mucus hyper-secretions and retention to help them clear the secretions from their lungs. The ACAPELLA O-PEP device combines the principles of low-frequency oscillation and positive expiratory pressure by employing a counterweighted lever and magnet to produce oscillatory positive pressures during expiration. This generated oscillating positive pressure works by mechanically reducing the viscoelasticity of the sputum by breaking down the bonds of mucus macromolecules which, in turn, enhances mucociliary clearance.

More recently it has been proposed to indicate the effectiveness of this therapy by placing a vibration sensor on the patient's chest, as described in PCT/GB2014/000220. In PCT/GB2014/000184, it is proposed to mount a vibration sensor on the casing of the therapy device to provide a signal indicative of use of the device. In PCT/GB2014/000177, it is proposed to use an external audio sensor, such as in a mobile phone, to monitor use of the device. These more recent proposals are mainly concerned with monitoring patient compliance.

The appropriate use of the O-PEP devices is critically dependent on the mechanical parameters of the pressure produced by the device, that is, the mean value of PEP, the frequency and amplitude of the generated oscillation. Typically, clinicians or respiratory therapists are responsible for selecting the appropriate airway clearance therapy for a particular patient ("The Value of Conducting Laboratory Investigations on Airway Clearance Devices," 2008; Respiratory Therapist Series, 1985; California Thoracic Society, 2006). They are also responsible for optimizing the operation of O-PEP devices to achieve the desired therapy goals (Hristara-Papadopoulou et al., 2008; California Thoracic Society, 2006; Myers, 2007).

These mechanical parameters, however, are dependent on the patient flow rate and the setting of the O-PEP device. Patients suffering from mucus hypersecretion and retention have various degrees of flow limitation. It has been observed that the mechanical parameters of the generated pressure vary across the spectrum of flow ranges, as shown in FIGS. 1A, 1B and 1C. The air flow/volume exhalation curve for patients using O-PEP devices is non-linear, as shown in FIG. 2. This, and the lack of any feedback to the patient makes it very difficult for the patient to maintain the flow rates prescribed by the clinician or respiratory therapist for the appropriate period.

It is an object of the present invention to provide alternative respiratory therapy apparatus and methods.

According to the present invention, there is provided respiratory therapy apparatus including a respiratory therapy device of the above-specified kind, characterised in that the apparatus includes pressure and flow sensors responsive to gas pressure and flow produced by the patient, and a processor connected to receive output signals of the pressure and flow sensors and arranged to correlate the output signals from the pressure and flow sensors with prescribed values, that the processor is arranged to provide an output to a feedback device in accordance with the extent to which the signals correlate with the prescribed values, and that the feedback device is arranged to be perceived by the patient to prompt him to adjust his use of the therapy device.

The device may include an actuator controlled by the output of the processor to adjust the position of a member arranged to control the setting of the therapy device. The member arranged to control the setting of the therapy device may be a rotatable dial. The feedback device may be arranged to produce a visual feedback and or alternatively an audible feedback and or alternatively a tangible feedback. The pressure and flow sensors may be located in the region of the breathing inlet of the therapy device. The processor preferably includes artificial intelligence software. The therapy device may include a rocker arm arranged to open and close an outlet during exhalation. The processor preferably is arranged to record the settings used for each therapy session.

Respiratory therapy apparatus according to the present invention will now be described, by way of example, with reference to the accompanying drawings, in which.

Figure 1A:
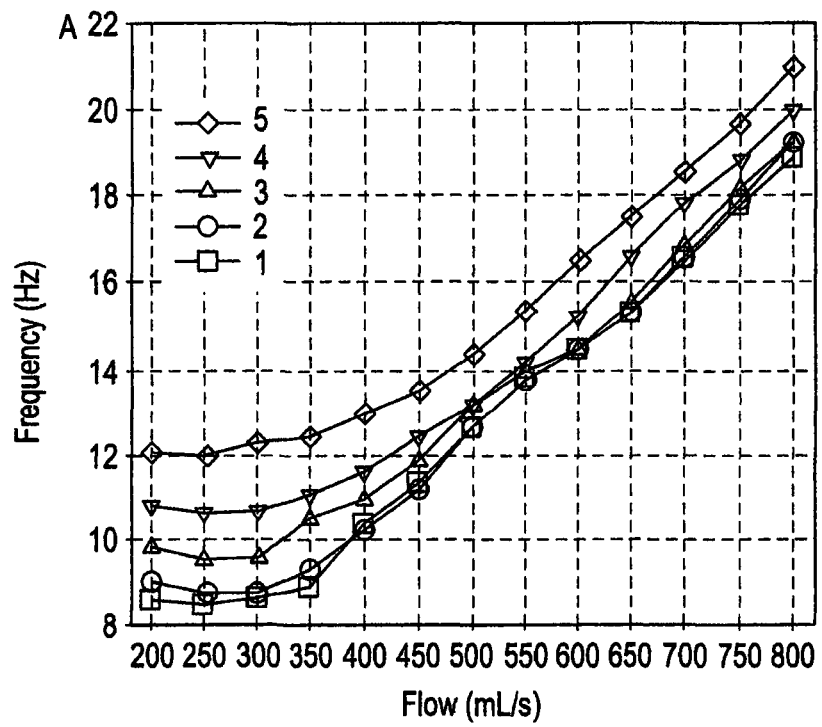
FIGS. 1A to 1C illustrate the mechanical behaviour of a prior art O-PEP devices over a range of flow rates.
Figure 1B:
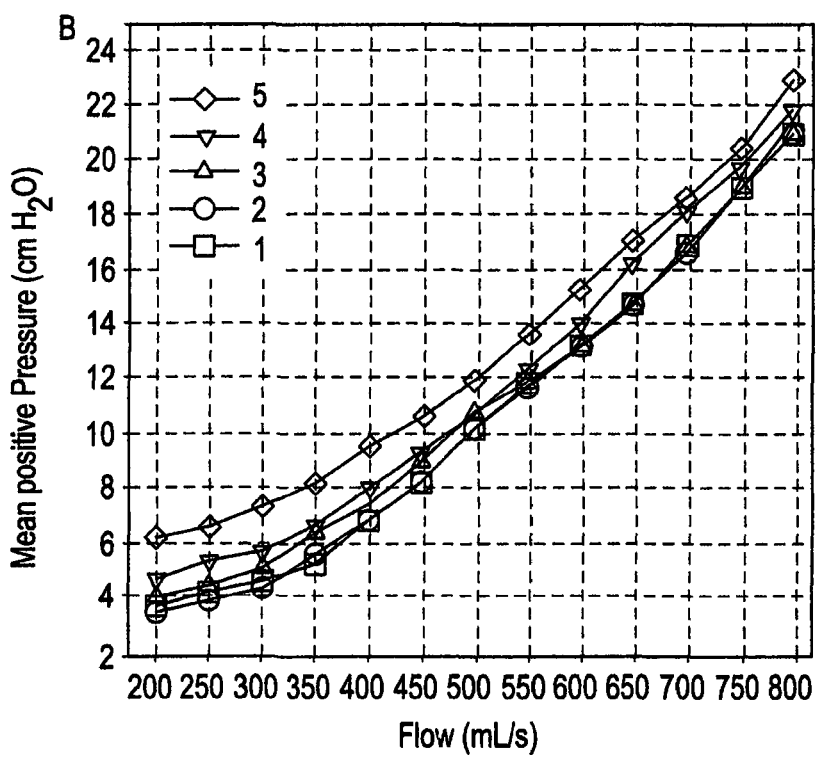
Figure 1C:
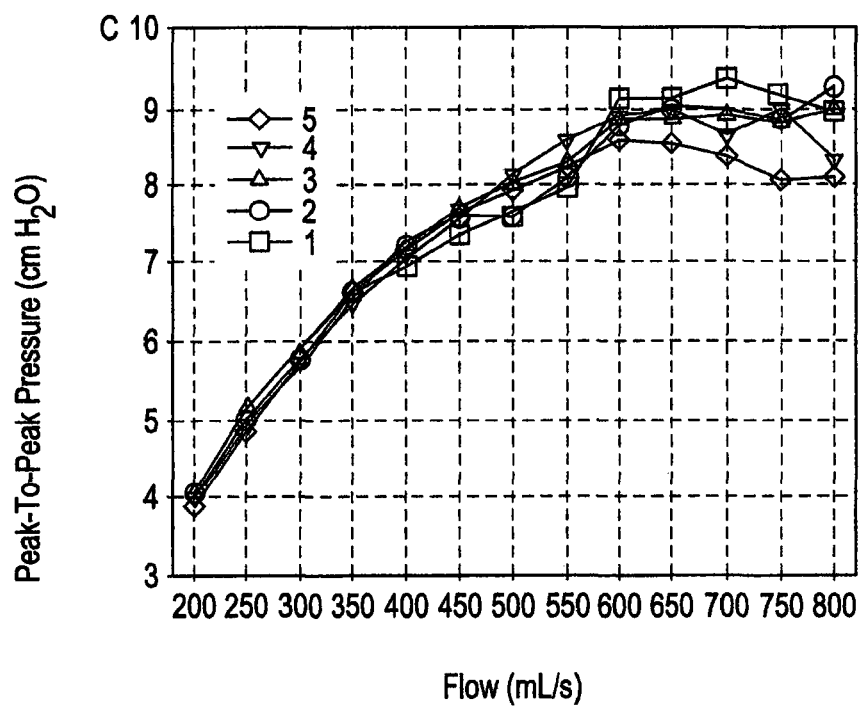
Figure 2:
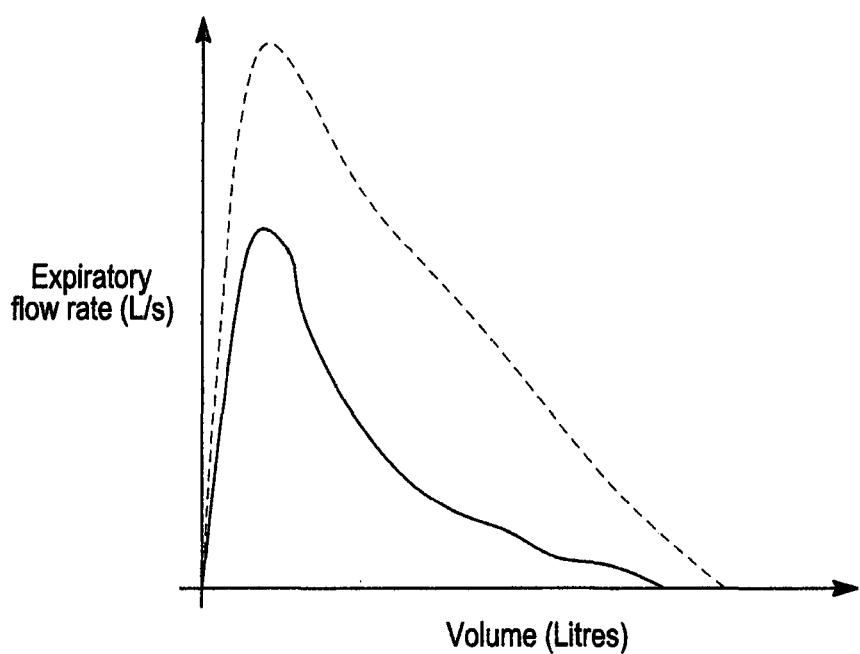
FIG. 2 illustrates the exhalation curve of prior art O-PEP devices.
Figure 3:
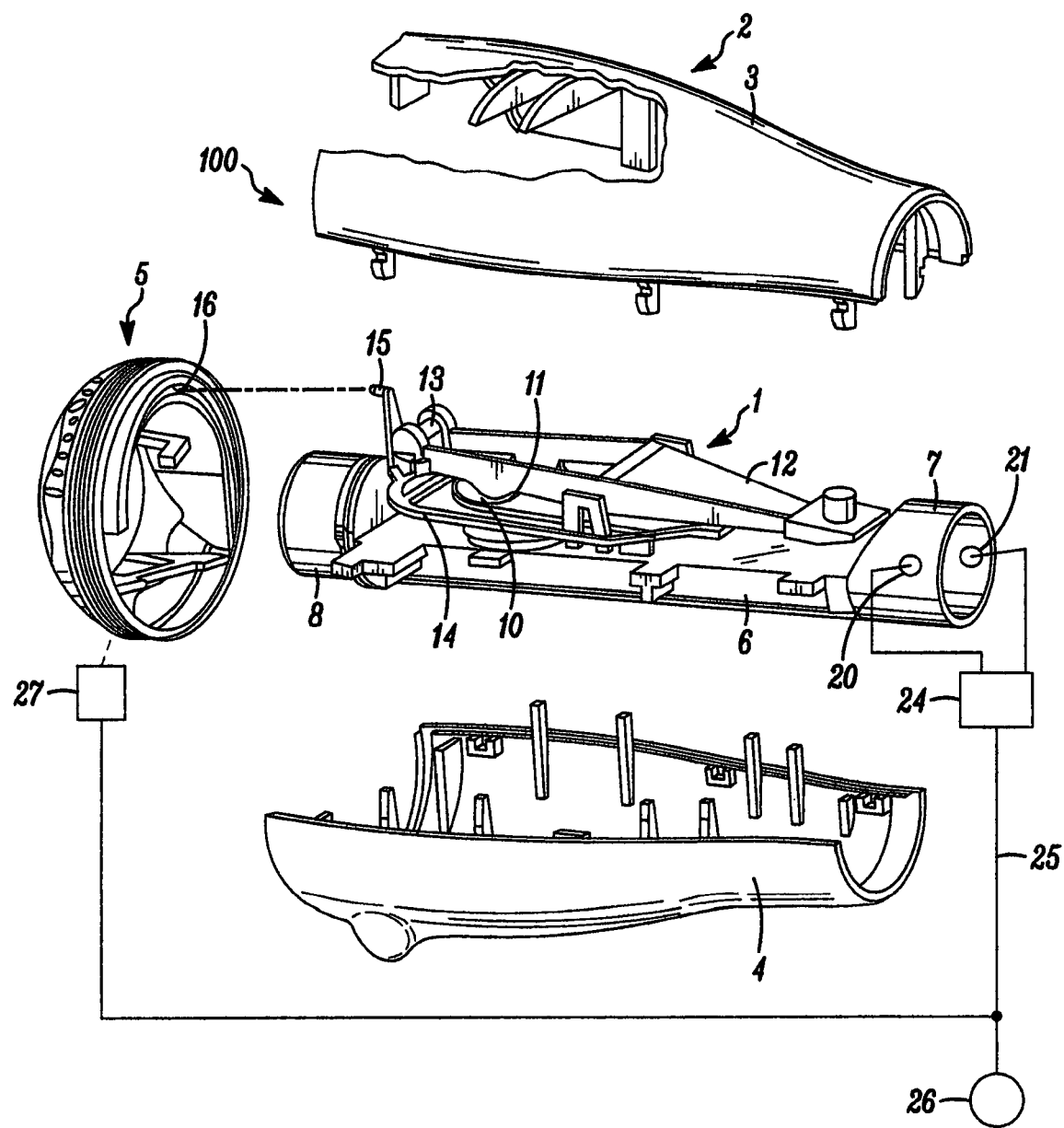
FIG. 3 illustrates the apparatus of the present invention.

With reference first to FIG. 3, the apparatus includes an "ACAPELLA" O-PEP device 100 comprising a rocker assembly 1 contained within an outer housing 2 provided by an upper part 3 and a lower part 4 of substantially semi-cylindrical shape. The device 100 is completed by an adjustable dial 5 of circular section. The rocker assembly 1 includes an air flow tube 6 with a breathing inlet 7 which may include or be coupled to a mouthpiece. An inspiratory inlet 8 at the opposite end includes a one-way valve (not shown) that allows air to flow into the air flow tube 6 but prevents air flowing out through the inspiratory inlet. The air flow tube 6 has an outlet opening 10 with a non-linear profile that is opened and closed by a conical valve element 11 mounted on a rocker arm 12 pivoted midway along its length about a transverse axis. The air flow tube 6 and housing 2 provide a structure with which the rocker arm 12 is mounted. At its far end, remote from the breathing inlet 7, the rocker arm 12 carries an iron pin 13 that interacts with the magnetic field produced by a permanent magnet (not visible) mounted on an adjustable support frame 14. The magnet arrangement is such that, when the patient is not breathing through the device, the far end of the rocker arm 12 is held down such that its valve element 11 is also held down in sealing engagement with the outlet opening 10. A cam follower projection 15 at one end of the support frame 14 locates in a cam slot 16 in the dial 5 such that, by rotating the dial, the support frame 14, with its magnet, can be moved up or down to alter the strength of the magnetic field interacting with the iron pin 13. The dial 5 enables the frequency of operation and the resistance to flow of air through the device to be adjusted for maximum therapeutic benefit to the user. Other O-PEP devices may have different setting arrangements for adjusting operation of the device and may be graduated in other ways, such as in frequency.

When the patient inhales through the breathing inlet or mouthpiece 7 air is drawn through the inspiratory inlet 8 and along the air flow tube 6 to the breathing inlet. When the patient exhales, the one-way valve in the inspiratory inlet 8 closes, preventing any air flowing out along this path. Instead, the expiratory pressure is applied to the underside of the valve element 11 on the rocker arm 12 causing it to be lifted up out of the opening 10 against the magnetic attraction, thereby allowing air to flow out to atmosphere. The opening 10 has a non-linear profile, which causes the effective discharge area to increase as the far end of the rocker arm 12 lifts, thereby allowing the arm to fall back down and close the opening. As long as the user keeps applying sufficient expiratory pressure, the rocker arm 12 will rise and fall repeatedly as the opening 10 is opened and closed, causing a vibratory, alternating or oscillating interruption to expiratory breath flow through the device. Further information about the construction and operation of the device can be found in U.S. Pat. No. 6,581,598.

The apparatus additionally includes a pressure sensor 20 and a flow sensor 21 mounted in the region of the breathing inlet 7 of the device 100 so that they are exposed to expiratory air flow upstream of the oscillating mechanism of the device. The pressure and flow sensors need not be separate, as shown, but could be incorporated into a single unit providing that information about both pressure and flow can be extracted from the output signals. The outputs from the sensors 20 and 21 are supplied to a processing unit 24 either by a wire connection (as shown) or by a wireless connection, such as with the Bluetooth protocol radio frequency transmission. The processing unit 24 may be mounted on the housing 2 of the O-PEP device 100 or remotely. The processing unit 24 preferably includes artificial intelligence software such as VISUALSTATE, VISSIM OR LABVIEW software.

The processing unit 24 produces a first output via a feedback channel 25 to a feedback device 26 that provides the user with feedback as to his use of the device. The feedback may confirm correct use or indicate incorrect use and how this might be mitigated, such as by breathing more forcefully or less forcefully, breathing for a longer or shorter period or altering the setting of the device. The feedback device could be of various different kinds, such as a visual device (typically a flashing light, a light of varying colour or intensity, or a moving needle or other element), an audible device (such as a buzzer, or a speaker via which spoken instructions are given to the user), or a tangible device (such as a vibrator or a braille tactile display) or any combination of these. The processing unit 24 may optionally also produce an output signal automatically to alter the setting of the device 100 such as to a settings adjustment actuator 27, which may incorporate a stepper motor, solenoid or other actuator to rotate the dial 5 or otherwise alter the position of a settings member.

Figure 4:
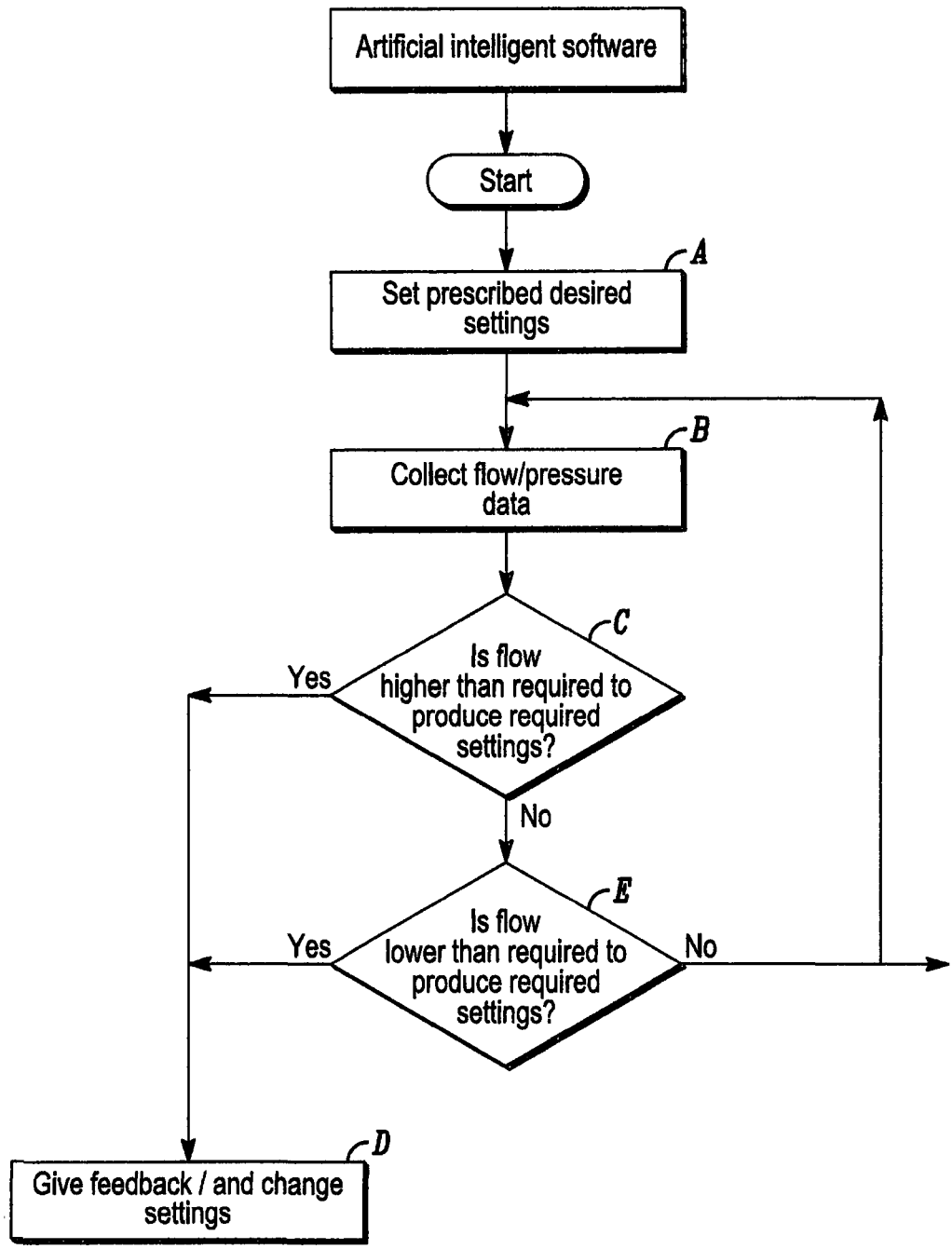
FIG. 4 is a flow chart showing operation of the apparatus.

Operation of the apparatus will now be described with reference also to FIG. 4. Initially, when the apparatus is first turned on, the processing unit 24 provides an output to the feedback device to recommend a setting (as indicated by box A) for the adjustable dial 5. Alternatively, where the apparatus includes an adjustment device 27 it may automatically set the adjustable dial 5 to the prescribed setting. The user then starts breathing through the device 100 so that flow and pressure data are collected, as indicated by box B. The software in the processing unit 24 now determines whether the flow and pressure are higher than required for the present setting, as indicated in box C. If the answer is Yes, the device gives the user feedback to change to a more appropriate setting or it automatically makes this change of setting, as indicated in box D. If the flow, however is not too high, the next step, as indicated in box E, is to determine if the flow is lower than required for the present setting. If the answer is Yes, the user is again given feedback or an automatic setting change is made, as shown in box D. If the flow is not higher than required, that is, the setting is correct for the user's breathing, the process returns to box B. In this way, use of the apparatus is continuously monitored and adjusted as the user changes the way in which he uses the O-PEP device. Furthermore, the user is given confidence that he is achieving maximum benefit from the respiratory therapy.

The present invention can be used to ensure that the apparatus is always at the most appropriate setting to achieve maximum therapeutic benefit for the user.

The apparatus preferably records in the processor the settings used for each therapy session since this could give an indication to the clinician of changes in the patient's clinical state that might require alternative or additional treatment.

The invention claimed is:

1. A respiratory therapy apparatus including: a therapy device having a breathing inlet that enables a patient to inhale and exhale through the therapy device and an oscillating mechanism movable to produce an oscillating resistance to breathing through the therapy device as long as sufficient expiratory pressure is applied to the oscillating mechanism by the patient during his exhalation breathing, the therapy device having a plurality of different operation settings, characterised in that the apparatus includes pressure and flow sensors responsive to gas pressure and flow produced by the patient, and a processor connected to receive output signals of the pressure and flow sensors and arranged to correlate the output signals from the pressure and flow sensors with prescribed values, that the processor is arranged to provide an output to a feedback device in accordance with the extent to which the output signals correlate with the prescribed values, and that the feedback device is arranged to provide a feedback signal to the patient to indicate to the patient that the patient is either correctly using the therapy device or that the patient is incorrectly using the therapy device to accordingly prompt the patient to adjust the patient's exhalation breathing through the therapy device; and the processor includes artificial intelligence software.

2. A respiratory therapy apparatus comprising: a therapy device having a breathing inlet that enables a patient to inhale and exhale along an air flow path through the therapy device; an oscillating mechanism mounted along the air flow path of the therapy device and arranged to be exposed to breathing by the patient, the oscillating mechanism is movable only by the breathing of the patient and arranged to produce an oscillating resistance as long as the patient keeps applying sufficient expiratory pressure during his exhalation breathing; adjustment means at the therapy device adapted to provide a plurality of different operation settings for the therapy device; pressure and flow sensors mounted to the therapy device to be responsive to gas pressure and flow produced by the breathing of the patient; a processor in communication with the pressure and flow sensors to receive output signals representative of the pressure and flow produced by the pressure and flow sensors, the processor correlating the output signals from the pressure and flow sensors with prescribed values to produce an output that is adapted to confirm correct use or indicate incorrect use of the therapy device by the user; and a feedback device in communication with the processor for receiving the output from the processor, the feedback device arranged to provide a feedback signal to the patient to inform the patient whether the patient is correctly using the therapy device, the feedback device further arranged to mitigate the patient's incorrect use of the therapy device by informing the patient to change the patient's breathing through the therapy device or to readjust the operation setting of the therapy device; and the processor includes artificial intelligence software.

\* \* \* \* \*